United States Patent [19]

Marvich

[11] 3,971,538

[45] July 27, 1976

[54] SURGICAL INSTRUMENT SUPPORT

[76] Inventor: Jack M. Marvich, 3516 Inwood Ave., New Orleans, La. 70114

[22] Filed: Sept. 16, 1975

[21] Appl. No.: 613,889

[52] U.S. Cl................................ 248/278; 248/122
[51] Int. Cl.² ..................... A47G 29/00; A47F 5/04
[58] Field of Search ........... 248/278, 279, 280, 281, 248/284, 291, 122; 403/162

[56] References Cited
UNITED STATES PATENTS

| 911,447 | 2/1909 | Roessler | 248/279 |
| 1,059,856 | 4/1913 | Fox | 248/283 X |
| 2,651,725 | 9/1953 | McFarland | 248/278 X |
| 3,193,674 | 7/1965 | Fleming | 248/278 X |
| 3,221,743 | 12/1965 | Thompson et al. | 248/279 X |
| 3,329,149 | 7/1967 | Kendall et al. | 248/278 X |

FOREIGN PATENTS OR APPLICATIONS 349,019  5/1905  France .............................. 248/279

Primary Examiner—J. Franklin Foss
Attorney, Agent, or Firm—Shoemaker and Mattare, Ltd.

[57] ABSTRACT

A device for holding surgical instruments so that they can be positioned at any desired orientation with respect to an operating table. The holding device comprises a sterilizable instrument holding hook which is detachably connected to one of a pair of pivotally connected, movable arms which have the other movable arm connected to a rotatable mounting means for mounting the device on the operating table. Brake or clutch means are interposed between the arms and between one arm and the mounting means for controlling the movement of the arms with respect to each other and with respect to the operating table.

5 Claims, 9 Drawing Figures

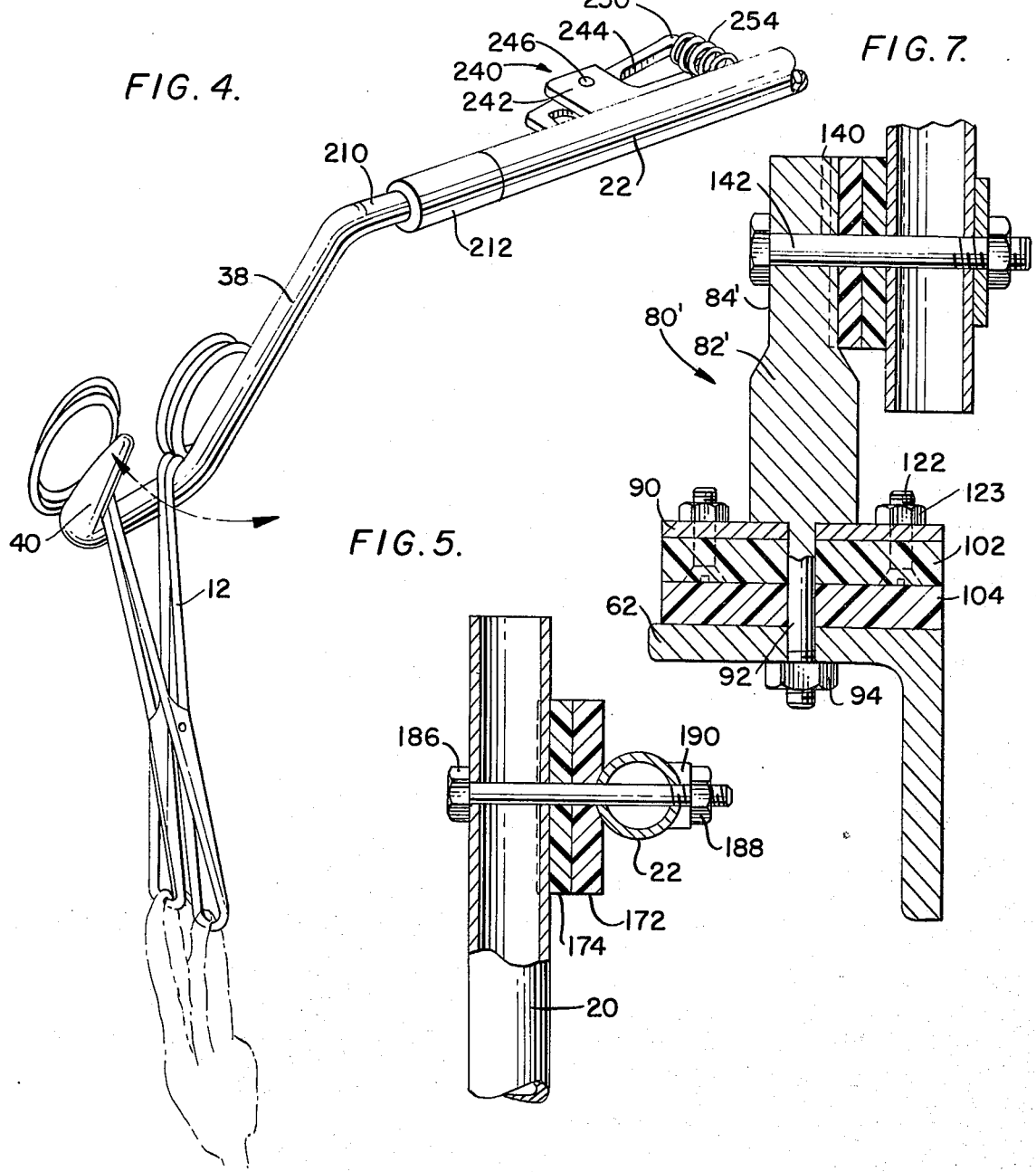

SURGICAL INSTRUMENT SUPPORT

BACKGROUND OF THE INVENTION

The present invention relates to surgical devices in general and, more particularly, to devices for supporting surgical instruments during a surgical operation.

When a surgeon performs an operation, it is often necessary to have a number of instruments, such as hemostats, retractors or forceps, supported adjacent the patient, and assistants or supporting devices can be used to maintain the instruments stationary. Thus, there are known instrument holding devices which can be set to perform the functions such as holding a retractor in a fixed position during an operation, or supporting electrical devices which may be employed during the operation. Some of these devices are adjustable and can support one or more instruments.

An instrument holding device, like the instruments themselves, must be stored between uses. Because of its proximity to the surgeon and patient during an operation, the instrument holding device should be as sterile as possible, for once a surgeon has sterilized for an operation, contact with an unsterile object may break the sterile field. Depending on where, and how, the instrument holding device is stored, the sterilization procedure can be quite complicated.

Furthermore, some surgeons, such as veterinary surgeons, may employ instrument holding devices quite often. It is therefore desirable to store the holding device in an assembled condition and in a convenient and accessible location.

However, because of the cooperation and configuration of the elements and members used to construct the known instrument holding devices, many must be disassembled for storage between uses. Some of the known devices need not be disassembled for storage, but these are often bulky and too large to be stored in areas where sterile conditions are maintained, and thus may not remain sterile during storage. Therefore, known devices, whether of the type which is stored in a knockdown condition, or of the type which is stored in the assembled condition, have the disadvantage of being inconvenient to store or have the disadvantage of requiring special assembly procedures to place them in a usable condition. Since it is undesirable to assemble or move such devices from a storage area after the operating room has been sterilized, operating room sterilization procedures must account for the instrument holding device and thus become that much more involved.

SUMMARY OF THE INVENTION

The device embodying the present invention can be stored in an assembled condition under the operating table and can be manipulated by the surgeon into any desired orientation with respect to the patient without requiring him to break the sterile field.

The preferred embodiment of the present invention comprises a clamping means for securing the device to an operating table, mounting means rotatably connected to the clamping means and positioned beyond one edge of the table, a pair of movable arms pivotally connected to each other and to the mounting means, a plurality of brake or clutch means for pivotally connecting the movable arms to each other and to the rotatable mounting means and controlling the movement of these elements with any desired degree of damping so that the force required to pivot the movable arms can be set according to the requirements of the operation, an autoclavable hook adapted to be detachably received in one end of one of the movable arms for supporting surgical instruments, and locking means for detachably locking the hook to that movable arm. The mounting means rotatably mounts the device to the clamping means so that the device is permitted to undergo rotational movement with respect to the table. The clutch means pivotally couple the arms together and to the mounting means so that those arms can pivot with respect to each other and with respect to the rotatable mounting means.

In the preferred embodiment, the clutch means each comprise discs mountable on the members with which the clutch is associated. The discs are arranged in facially opposed pairs so that when the members are coupled together with the brake therebetween, a frictional coupling exists between those members. Thus, the movable arms are associated with each other and with the mounting means via the discs. The discs permit the movable arms to undergo a full 360° rotation with respect to each other and with respect to the mounting means which is positioned adjacent the end of the operating table. The movable arms therefore can easily be manipulated during the operation, and then folded into a coextensive orientation and moved into a storage position near the operating table for storage after the operation is completed.

In the preferred embodiment, the instrument supporting hook is formed of autoclavable material and is autoclaved along with the surgical instruments. The hook is locked into the free end of an upper movable arm by the surgeon and can then be used as a "handle" for manipulating the instrument holding device and orienting it into the desired position with respect to the table and/or the patient. Manipulating the holding device using the autoclaved hook enables the surgeon to orient the device without breaking the sterile field. Furthermore, insertion of the autoclaved hook into the holding device does not require the surgeon to touch any unsterile members and thereby cause him to contaminate his sterile gloved hand.

OBJECTS OF THE INVENTION

Accordingly, it is a main object of the present invention to enable a surgeon to have instruments held at any desired location during an operation without requiring an assistant.

A further object of the present invention is to enable a surgeon to mount an instrument holding element onto an instrument holding device without breaking the sterile field.

It is yet another object of the present invention to enable a surgeon to manipulate an instrument holding device without breaking the sterile field.

It is still another object of the present invention to provide a device which is storable without requiring disassembly thereof.

It is still a further object of the present invention to provide an instrument holding device which can be easily manipulated, and the movements of which are easily controlled.

These and other objects of the present invention, along with further advantages thereof, can be understood and appreciated by those skilled in the surgical arts with reference to the following description and appended claims, together with the accompanying drawings of which:

FIG. 3 shows the details of the detachable connection between an instrument holding hook and one arm of the instrument holding device;

FIG. 4 shows further details of the instrument holding hook;

FIG. 5 shows details of one of the brake means embodying the teachings of the present invention;

FIG. 7 shows details of another embodiment of the upright support member;

DESCRIPTION OF A PREFERRED EMBODIMENT

Figure 1:
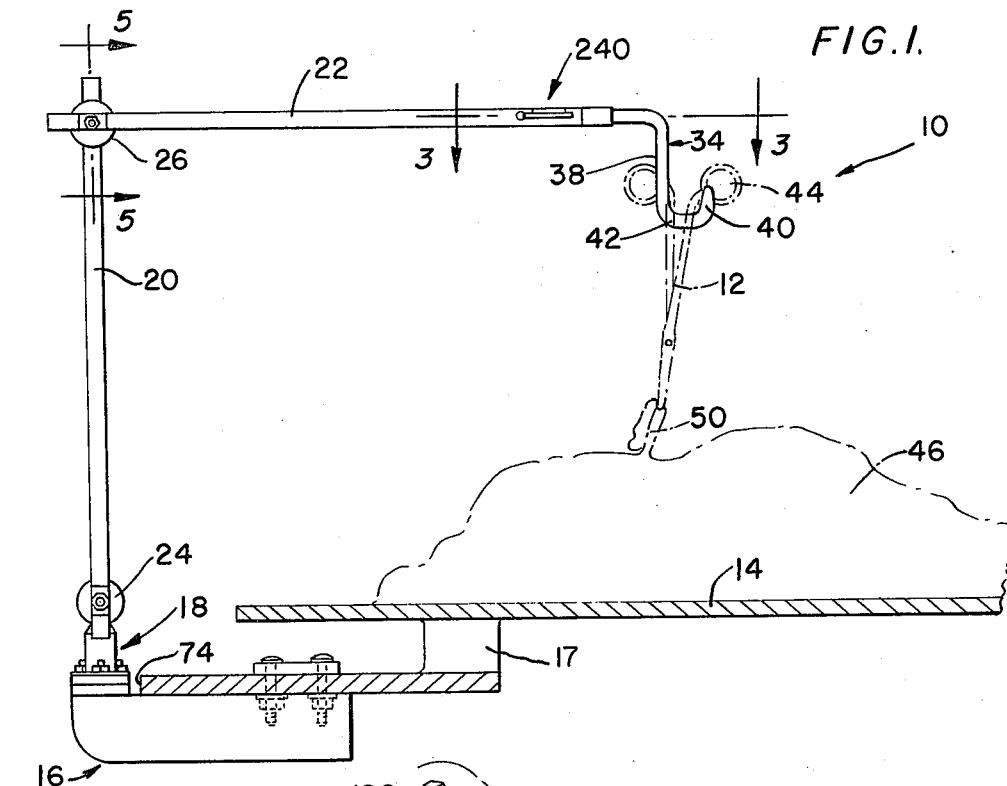
FIG. 1 shows the instrument holding device oriented above a patient in accordance with the teachings of the present invention.
Figure 2:
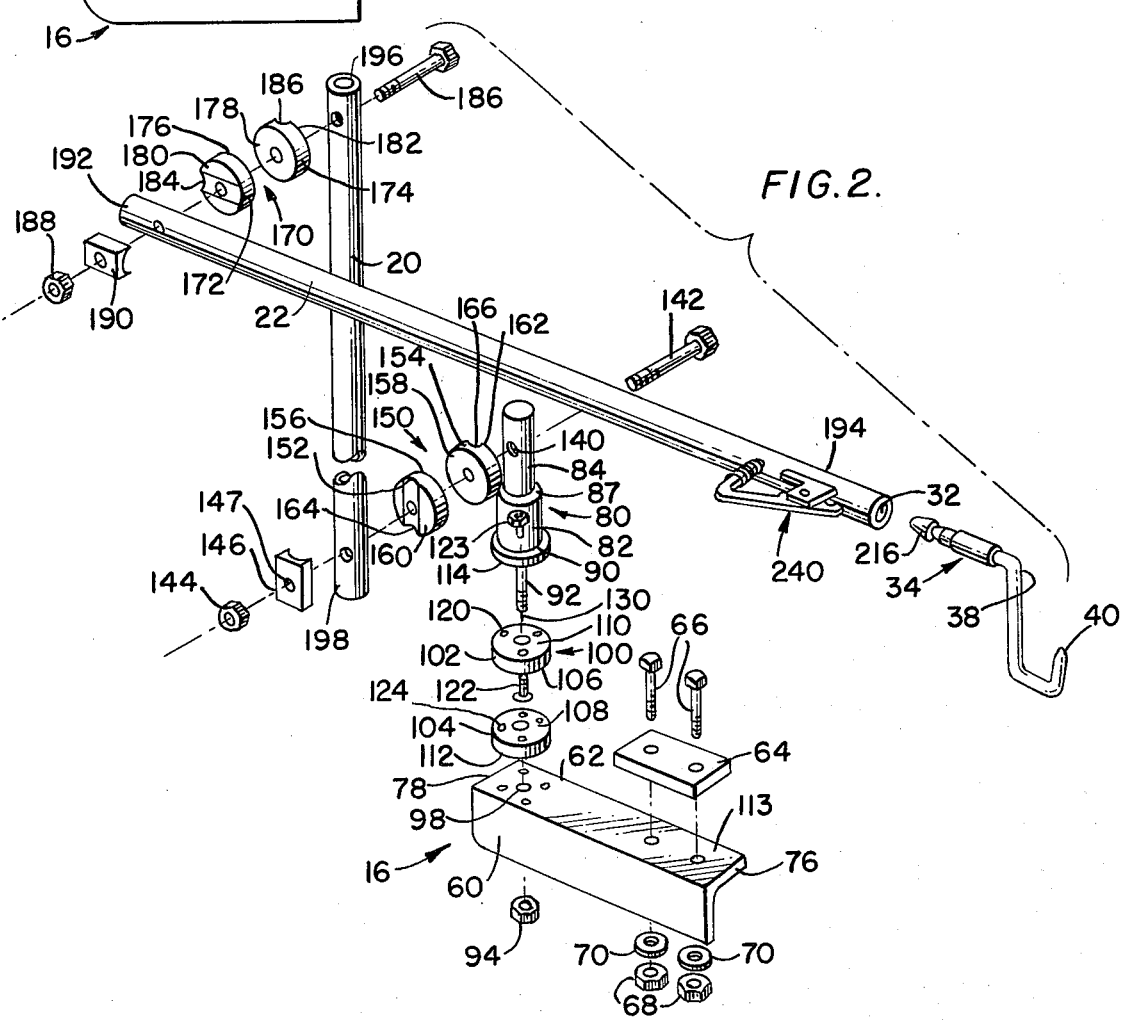
FIG. 2 is an exploded, perspective view of the instrument holding device embodying the present invention.

Shown in FIG. 1 is a device for holding instruments during surgery, in particular veterinary surgery. The apparatus is generally indicated by the reference numeral 10. The apparatus is also shown in FIGS. 2, 3 and 4. As shown in FIG. 1, the apparatus 10 can be used to support one or a plurality of surgical instruments, such as a hemostat 12, and is supported under a table 14, such as a standardized veterinary surgical table, by a clamping means 16 attached to table element 17, such as a standard horizontal bar of a veterinarian table about which portions of the table pivot. The apparatus 10 comprises a rotatable base 18 and a pair of movable arms 20 and 22 pivotally connected to the rotatable base and to each other by brakes or clutches 24 and 26, respectively. In the preferred embodiment, the arms are of equal length. The movable arm 22 has an axial bore 32 (FIG. 2), and is connected at one end to brake 26. In the preferred embodiment, a U-shaped hook 34 serves as an instrument supporting means and is detachably received in the other end of movable arm 22 by interfitting it into the axial bore 32. The hook 34 has a long leg 38 and a short leg 40 connected by bight 42. As shown in FIG. 1, an instrument, such as hemostat 12, is supported by hook 34 through engagement of finger grips 44 against the legs and bight of the hook. As shown, the instrument can be used to support a portion of a patient 46, such as a vein 50.

FIG. 2 shows an exploded, perspective view of the apparatus 10. As shown in FIG. 2, the clamping means 16 comprises an L-beam base having legs 60 and 62, and a plate 64 which can be secured to the leg 62 by bolts 66 attached to nuts 68 and fitting through washers 70. The base can also be a flat plate. The plate 64 clamps to the underneath frame of the table in such a manner as to lower the clamping means near the table height for easy storage. The table edge 74 (FIG. 1) is positioned intermediate ends 76 and 78 of leg 62. As will be discussed below, the positioning of table edge 74 intermediate leg ends 76 and 78 enables the device 10 can be easily stored.

Figure 6:
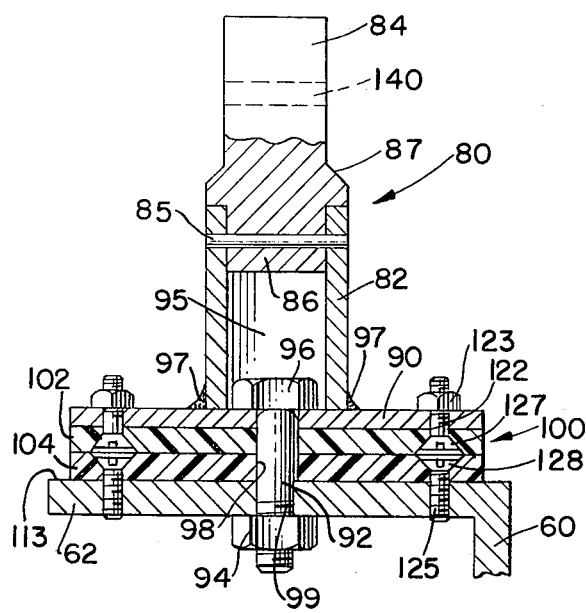
FIG. 6 shows details of the mounting means of the device embodying the teachings of the present invention.

An upright support member 80 is mounted on leg 62 adjacent end 78 thereof. As shown in FIGS. 2 and 6, support member 80 comprises two cross-pinned tubular elements which include a hollow base portion 82 and a projection 84 connected thereon by a pin 85 fitting through holes in the upper end of base portion 82 and tail 86 of the projection 84. Base portion 82 and projection 84 are cylindrical, with projection 84 having a smaller diameter than that of base portion 82 so that a shoulder 87 is formed between the base portion 82 and the projection 84. The support member 80 further comprises a flange 90 positioned around the end of base portion 82 which is remote from shoulder 87. A bolt 92 is attachable to leg 62 by nut 94. As shown in FIG. 6, the base portion 82 is hollow to form an axial bore 95 into which head 96 of the bolt 92 is received. A weldment or other suitable attaching means 97 secures base portion 82 to flange 90. The base portion 82 can therefore rotate while bolt 92 remains fixed. Bolt 92 fits through a hole 98, having a flat face 99, in the leg 62 and head 96 has a flat surface which cooperates with the flat surface of leg 62 adjacent hole 98 to maintain bolt 92 fixed in position. Inserted between flange 90 and the top surface of leg 62 is a mounting means 100 comprising a pair of discs 102 and 104. The discs have faces 106 and 108 and rear surfaces 110 and 112, respectively. As seen in FIGS. 1, 2 and 6, faces 106 and 108 are in opposed, contactable relationship with each other. As shown in FIG. 2, rear surface 110 of disc 102 is in opposed, contactable relationship with undersurface 114 of flange 90, and surface 112 of disc 104 is in opposed, contactable relationship with top surface 113 of leg 62 of clamping means 16. The discs each have an axial hole through which bolt 92 interfits when the upright support member 80 is coupled to leg 62. Furthermore, disc 102 has a plurality of bolt holes 120 through which screws 122 interfit and are threadably engaged by nuts 123 to attach disc 102 to flange 90 of the support member 80, and disc 104 has a plurality of bolt holes 124 through which screws 125 interfit and are threadably engaged in top surface 113 of leg 62. The screws 122 and 125 have heads 127 and 128, respectively, seated in countersink holes in discs 102 and 104, respectively, so that discs 102 and 104 can rotate with respect to each other and surfaces 106 and 108 can move freely on each other.

Because disc faces 106 and 108 are in sliding contact with each other, support member 80 is roatatably attached to clamping means 16. Therefore, support member 80 can undergo rotation with respect to the central axis 130 thereof in either direction.

Projection 84 has a radially directed hole 140 therethrough which receives a bolt 142 for coupling movable arm 20 to support member 80. A nut 144 is threaded onto bolt 142 to effect this coupling, and a channeled washer 146 assures that bolt 142 provides a secure attachment of arm 20 to projection 84. Discs 102 and 104, like the clutch means to be discussed below, can have a friction surface interposed between the opposed faces thereof. The channeled washer is positioned between nut 144 and arm 20 to assure that nut 144 will not loosen as arm 20 is rotated. Channeled washer 146 has a flat sided hole 147, and bolt 142 has one flat side which cooperates with the flat sided hole 147 to prevent nut 144 from becoming loose when arm 20 is rotated.

Supporting means 80' is an alternative embodiment of the supporting means and is shown in FIG. 7. Bolt 92 depends from the base portion 82'. As shown in FIG. 7, disc 102 is attached to flange 90 by screws 122 and nuts 123, and disc 104 is captured between disc 102 and leg 62 by the bolt 92. The bolt 142 fits through a hole 140 in projection 84'. The alternative embodiment of the supporting means is a solid piece of cast metal.

Interposed between arm 20 and projection 84 is a first clutch means 150. First clutch means 150 comprises a pair of discs 152 and 154 having opposed faces 156 and 158, respectively, and grooved rear surfaces 160 and 162, respectively. Thus, as shown in FIG. 2, rear surface 160 has a groove 164 defined therein to cooperate with arm 20, and rear surface 162 of disc 154 has defined therein a groove 166 which cooperates with projection 84 so that when the arm 20 is secured to projection 84 with the clutch means 150 therebetween, disc 152 is movable with arm 20 and disc 154 remains stationary with respect to projection 84. Opposed faces 156 and 158 are in frictional contact so that arm 20 can pivot about bolt 142 and hence move in a vertical plane with respect to table 14. Thus, arm 20 is pivotably coupled to a base which rotates with respect to the table, and the instrument supporting means has at least two degrees of freedom. The amount of friction generated between faces 156 and 158 is adjusted by the amount of take-up applied to nut 144 on bolt 142. Therefore, the amount of torque required to pivot arm 20 about bolt 142 is adjusted according to the requirements to be placed on the apparatus 10. Such requirements are, for example, weight of the appendage to be supported by the instrument, ease of movement of arm 20, and the like.

On the end of arm 20 which is remote from that end connected to the first clutch means is located a second clutch means 170. Clutch means 170 is similar to first clutch means 150 and comprises coacting discs 172 and 174 having opposed faces 176 and 178, as well as grooved rear surfaces 180 and 182, which have grooves 184 and 186 defined therein to cooperate with the movable arms to provide a controlled relative rotation between the two movable arms. The arms, with the second clutch means interposed therebetween, are connected by bolt 186 cooperating with nut 188 and channeled washer 190. Thus, the second clutch means provides the instrument supporting means with still another degree of freedom. The instrument support means thus has at least three degrees of freedom.

The second clutch means, like the first clutch means, provides a controlled relative rotation between two members, in this case movable arms 20 and 22, according to the amount of friction produced by the contact between opposed faces 176 and 178. As in the case of the first clutch means, this frictional engagement is controlled according to the take-up of nut 188 on bolt 186, and is subject to considerations which are similar to those used in determining the amount of take-up of nut 144 on bolt 142.

By referring to FIGS. 1 and 2, it is seen that the clutch means, together with the mounting means 100, enables the surgeon to adjust the instrument supporting means into any desired position with respect to the patient. By rotating the support member 80, pivoting arm 20 with respect to the support member, and/or pivoting arm 22 with respect to arm 20, the surgeon can set hook 34 in any desired orientation with respect to the patient. Furthermore, upon completion of an operation, the arms 20 and 22 can be oriented into a coextensive folded condition, wherein ends 192 and 194 of arm 22 are adjacent ends 196 and 198 of arm 20, and arm 20 is rotated to a position so that the arm 20 can be rotated with respect to the projection 84 to rotate the folded arms so that the apparatus 10 can be stored adjacent table 14 between uses. Therefore, the apparatus 10 can be stored adjacent table 14 without requiring disassembly thereof. Furthermore, as shown, the clutches and the mounting means permit a relative rotation of 360 degrees, thus enhancing the adaptability of the apparatus 10.

The clutch means, along with the mounting means, are shown in the assembled condition in FIGS. 5 and 6. The brake discs can be constructed of Micarta, or other suitable material, and the mounting discs can be constructed of nylon, or other suitable material.

As shown in FIGS. 3 and 4, hook 34 is detachably received in end 194 of arm 22. Hook 34 comprises a shank 210, a trunk 212, a frusto-conical neck 214, a conical locking head 216, and a shoulder stop 217 which cooperates with terminal edge 218 of the arm 22. As shown in FIG. 3, the frustum of neck 214 is smaller in diameter than the diameter of the locking head 216, which is approximately equal to the inner diameter of bore 32, and therefore forms a ledge 219 on the rear surface of head 216. The ledge 219 is used to lock the hook into the bore of arm 22. In the preferred embodiment, the outer surface of arm 22 adjacent the terminal end thereof is smooth. Thus, hook 34 freely rotates and automatically orients itself in the direction of the pull exerted thereon. The rotational movement of hook 34 is indicated in FIG. 3 by dotted and solid lines and by arrow 220. Hook 34 is maintained in engagement with arm 22 by locking means 240 which comprises support member 242 mounted on the outside of arm 22 and lever arm 244 pivotally connected to support member 242 by pivot pin 246. Lever arm 244 comprises, on one end, a finger 248, and on the other end, a prong 250. Both finger 248 and prong 250 are disposed toward arm 22, and finger 248 is arranged to fit through an access hole 252 to extend radially inward of arm 22. Prong 250 is longitudinally received in one end of a compression spring 254 which is mounted at its other end onto the outer surface of arm 22. As shown in FIG. 3, compression spring 254 urges prong 250 radially outward from arm 22 so that lever arm 244 pivots about pivot pin 246, thereby forcing finger 248 into access hole 252, and into engagement with ledge 219 of hook 34 to lock hook 34 to arm 22. To release hook 34 from arm 22, the lever arm 244 is depressed into the position indicated by dotted lines in FIG. 3, thereby moving finger 248 out of locking engagement with the ledge 219 of hook 34. Once finger 248 is moved out of locking engagement with ledge 218, hook 34 can be withdrawn from engagement with arm 22. As shown in FIG. 3, the compression spring 254 is arranged to maintain the finger 248 in the locking position shown in solid lines. As locking head 216 is conically shaped, the lever arm need not be pivoted in order to insert the hook into arm 22.

The hook 34 is manufactured of an autoclavable stainless steel. Therefore, the hook can be autoclaved along with the general surgical instruments. Upon commencement of surgery, the surgeon opens the sterilized instrument pack, removes a sterilized hook and inserts it into arm 22. The surgeon can then move the hook into virtually any desired position above the patient. The hook can then be used to support surgical instruments and thus eliminate the need for an assistant. Since the hook has been sterilized along with the instruments, the surgeon can handle the hook without contaminating his sterile gloved hand. Furthermore, by grasping the hook to move it into the desired position, the surgeon can properly and easily manipulate the apparatus 10 to orient the hook without breaking the sterile field.

Figure 8:
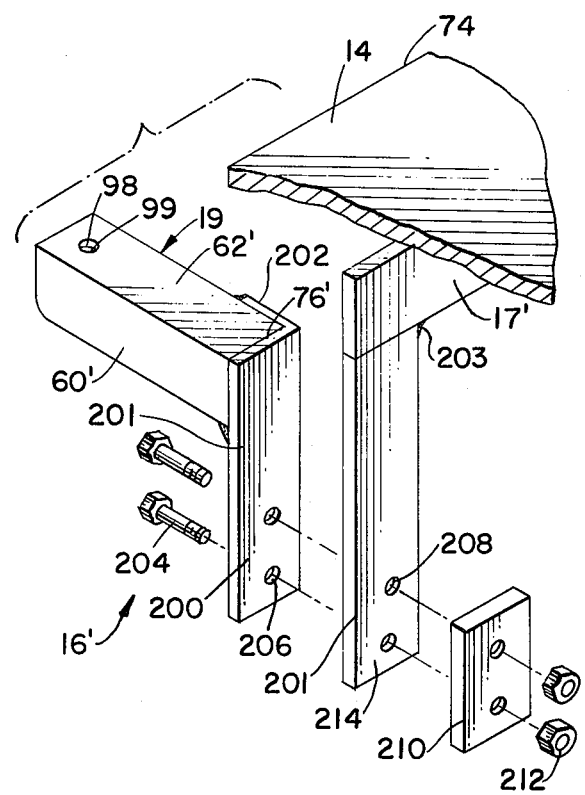
FIG. 8 shows details of a clamping means used in conjunction with the device shown in FIG. 1.
Figure 9:
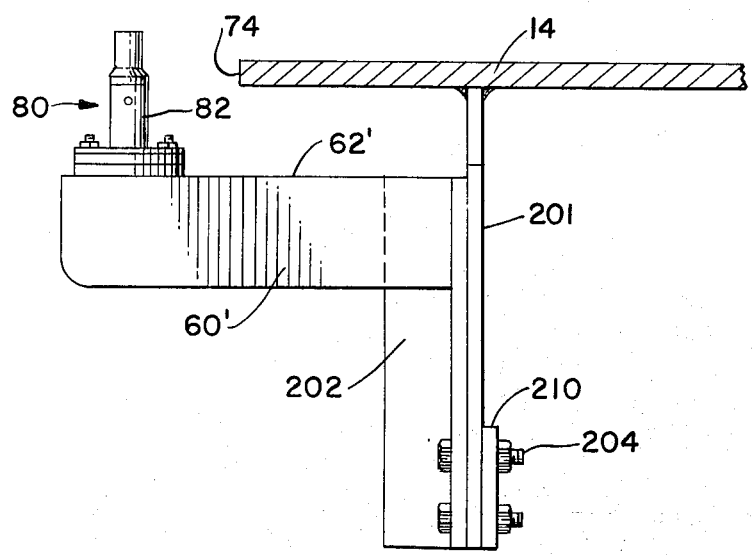
FIG. 9 shows the FIG. 8 clamping means attached to a table.

Another form of clamping means 16 is shown in FIGS. 8 and 9 as 16'. The clamping means 16' comprises an L-shaped member 19 having a side leg 60' and a top leg 62' connected at end 76' to an L-shaped bar 200 having legs 201 and 202. The bar 200 is attached to a mounting element 201 which depends from a table element 17' and is attached thereto by suitable securing means, such as weldments 203. Bolts 204 fitting through oblong holes 206 in bar 200 and holes 208 in mounting element 201 and threadably engaging nuts 212 clamp a plate 210 to surface 214 of the mounting element 201 to secure the clamping means 16' to the table 14, as shown in FIG. 9. The oblong holes 206 allow movement to compensate for variations in thickness of the bar 200. The mounting means 80 of device 10 can be mounted on leg 62' of the mounting means 16' in a manner which is similar to the manner in which the device 10 is mounted on clamping means 16 in which a bolt fits through hole 98 in leg 62' to attach base portion 82 to the clamping means.

The apparatus 10, as above-described, has been used to support a 10 pound weight at the end of the hook. Such a weight is approximately equal to that of a limb of a small animal.

AS this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:
1. A device for holding surgical instruments, comprising:
    clamping means attached to a table;
    mounting means rotatably attached to said clamping means so that said mounting means can be rotated with respect to said table;
    a first movable arm having two ends and pivotally connected at one end to said mounting means;
    a first brake means connecting said first movable arm at said one end to said mounting means to provide selectively adjustable pivotal engagement between said first movable arm and said mounting means, said first brake means including a pair of facially engaged discs located between said mounting means and said first movable arm one end, each disc having a groove defined in a rear surface thereof in which an outer surface of said first movable arm and said mounting means are respectively engaged;
    a second movable arm having two ends and pivotally connected at one end to the other end of said first movable arm, said second movable arm having a longitudinal bore in the other end thereof;
    a second brake means connecting said second movable arm one end to the other end of said first movable arm to provide selectively adjustable pivotal engagement between said first and second movable arms, said second brake means including a pair of facially engaged discs located between said second movable arm one end and said first movable arm other end, each disc having a groove defined in a rear surface thereof in which an outer surface of said first and second movable arms are respectively engaged;
    an instrument supporting hook detachably mounted on said other end of said second movable arm for supporting surgical instruments, said instrument supporting hook being formed of an autoclavable material; and
    locking means on said second movable arm including a lever pivotally mounted on said second arm and having a finger on one end thereof adapted to fit into an access hole in said second arm, and biasing means mounted on said second arm and attached to said lever to bias said finger into said access hole for releasably engaging said supporting hook, to detachably lock said hook to said second movable arm.

2. The device of claim 1, further including bolts for connecting said movable arms together and to said mounting means.

3. The device of claim 1, wherein said movable arms are pivotal through an angle of 360° with respect to each other.

4. The device of claim 1, wherein said mounting means is rotatable through an angle of 360° with respect to said table.

5. The device of claim 1, wherein said hook is U-shaped, with one leg shorter than the other.

* * * * *